(12) United States Patent
Chen et al.

(10) Patent No.: US 9,433,414 B2
(45) Date of Patent: Sep. 6, 2016

(54) LINEAR CUTTING STAPLER

(75) Inventors: Wangdong Chen, Jiangsu (CN); Tuo Shu, Jiangsu (CN); Yongwang Pei, Jiangsu (CN)

(73) Assignee: TOUCHSTONE INTERNATIONAL MEDICAL SCIENCE CO., LTD, Jiangsu (CN)

( * ) Notice: Subject to any disclaimer, the term of this patent is extended or adjusted under 35 U.S.C. 154(b) by 523 days.

(21) Appl. No.: 13/991,535

(22) PCT Filed: Nov. 29, 2011

(86) PCT No.: PCT/CN2011/083111
§ 371 (c)(1),
(2), (4) Date: Jun. 4, 2013

(87) PCT Pub. No.: WO2012/075895
PCT Pub. Date: Jun. 14, 2012

(65) Prior Publication Data
US 2013/0264372 A1 Oct. 10, 2013

(30) Foreign Application Priority Data
Dec. 10, 2010 (CN) .......................... 2010 1 0581557

(51) Int. Cl.
*A61B 17/068* (2006.01)
*A61B 17/072* (2006.01)
*A61B 17/32* (2006.01)

(52) U.S. Cl.
CPC ......... *A61B 17/068* (2013.01); *A61B 17/0682* (2013.01); *A61B 17/07207* (2013.01);
(Continued)

(58) Field of Classification Search
CPC .......... A61B 2017/07271; A61B 2017/07278
USPC ........................................... 227/175.2, 175.3
See application file for complete search history.

(56) References Cited

U.S. PATENT DOCUMENTS 4,892,244 A    1/1990   Fox et al.
5,129,570 A *  7/1992   Schulze .......... A61B 17/07207
                                              227/175.2
(Continued)

FOREIGN PATENT DOCUMENTS

CN    2764312 Y    3/2006
CN    2880397 Y    3/2007
(Continued)

OTHER PUBLICATIONS

International Search Report for International application No. PCT/CN2011/083111, Mar. 1, 2012, with English translation.
(Continued)

*Primary Examiner* — Stephen F Gerrity
*Assistant Examiner* — Joshua Kotis
(74) *Attorney, Agent, or Firm* — Cantor Colburn LLP

(57) ABSTRACT

A linear cutting stapler comprises: an upper jaw and a lower jaw (1) capable of closing or opening relative to each other. A staple cartridge (2) is disposed at a distal end of the lower jaw (1). The lower jaw (1) has a U shape, in which a striker (5) and a pushing rod are slidably disposed. The linear cutting stapler further comprises a safety mechanism. The safety mechanism comprises a safety piece (4), and an opening (52) opened on the striker (5) and for receiving the safety piece. The installation or removal of the staple cartridge (2) may drive the safety piece (4) to move in a direction perpendicular to the axis of the lower jaw (1), so that the safety piece (4) is disengaged from or engaged with the opening (52) of the striker (5). The linear cutting stapler has a simple structure, can be easily fabricated, and is safe and reliable.

6 Claims, 4 Drawing Sheets

(52) U.S. Cl.
CPC ............... *A61B2017/07271* (2013.01); *A61B 2017/07278* (2013.01); *A61B 2017/07285* (2013.01); *A61B 2017/320052* (2013.01)

(56) References Cited

U.S. PATENT DOCUMENTS

| | | | | |
|---|---|---|---|---|
| 5,364,001 | A * | 11/1994 | Bryan | A61B 17/07207 227/175.1 |
| 5,462,215 | A * | 10/1995 | Viola | A61B 17/072 227/176.1 |
| 5,673,842 | A * | 10/1997 | Bittner | A61B 17/07207 227/175.2 |
| 5,988,479 | A | 11/1999 | Palmer | |
| 7,055,730 | B2 | 6/2006 | Ehrenfels et al. | |
| 7,328,828 | B2 * | 2/2008 | Ortiz | A61B 17/07207 227/175.2 |
| 2004/0007608 | A1 | 1/2004 | Ehrenfels et al. | |
| 2005/0173490 | A1 | 8/2005 | Shelton, IV | |
| 2005/0222616 | A1 * | 10/2005 | Rethy | A61B 17/07207 606/215 |
| 2007/0119900 | A1 * | 5/2007 | Ehrenfels | A61B 17/07207 227/176.1 |
| 2009/0134199 | A1 | 5/2009 | Heinrich | |

FOREIGN PATENT DOCUMENTS

| | | |
|---|---|---|
| CN | 201160868 Y | 12/2008 |
| CN | 201160870 Y | 12/2008 |
| CN | 101416895 A | 4/2009 |
| CN | 101675895 A | 3/2010 |
| CN | 101991453 A | 3/2011 |
| CN | 201949071 U | 8/2011 |
| EP | 0488768 A1 | 11/1991 |
| JP | 2007125396 A | 5/2007 |
| JP | 2007252952 A | 10/2007 |
| JP | 2010372 A | 1/2010 |
| WO | 9523557 A1 | 9/1995 |

OTHER PUBLICATIONS

Extended European Search Report for International App. No. 11846162.3-1654; Dated May 9, 2014; 7 pages.

Office Action for the Japanese Patent No. 2013-542353, Mailed on May 7, 2014. English Translation Attached.

* cited by examiner

LINEAR CUTTING STAPLER

The present application claims the benefit of priority to Chinese Patent Application No. 201010581557.0 titled "LINEAR CUTTING STAPLER" and filed with the State Intellectual Property Office on Dec. 10, 2010, the entire disclosure of which is incorporated herein by reference.

FIELD OF THE INVENTION

The present application relates to a linear cutting stapler, which belongs to the technical field of medical instruments.

BACKGROUND OF THE INVENTION

Linear cutting staplers are widely used in surgical operations for wound closure, and internal tissue closure and excision. A typical linear cutting stapler as disclosed in U.S. Pat. No. 5,129,570 performs two functions of stapling and cutting, to remove the redundant tissue while stapling the wound. This kind of linear cutting stapler generally includes two jaws (i.e., an upper jaw and a lower jaw), a closing handle for closing the upper jaw and the lower jaw, a staple anvil and a staple cartridge arranged opposite to each other at the front ends of the upper jaw and lower jaw respectively, a firing piece and a cutter which are arranged in the staple cartridge and are moveable synchronously relative to the staple cartridge, and a push button for driving movement of the firing piece and the cutter. Staples are arranged in the staple cartridge. The firing piece pushes a staple pusher successively and pushes the staples towards the staple anvil. The cutter cuts off the tissue between the staple cartridge and the staple anvil.

The staple cartridge of the instrument can be used for multiple times by being replaced. In clinical application, multiple times of stapling and cutting tissues are often required, and thus the staple cartridge is required to be replaced for many times in an operation. When no staple cartridge is loaded, the push button can be pushed forwards arbitrarily, and then the cutter may be pushed out. This may cause serious consequence as arising from only cutting without stapling. Accordingly, a safety mechanism is provided in the linear cutting staplers in the prior art.

The U.S. Pat. No. 5,129,570 discloses a safety mechanism, in which a safety block with a cutter passage and a staple pushing bar passage is provided in the middle portion of the instrument, and a leaf spring is provided under the cutter. When the instrument is in an opened position, i.e., the upper jaw and the lower jaw are not closed, the leaf spring lifts the cutter upwards, so that the cutter cannot pass through the cutter passage, thereby playing the role of safety. After the staple cartridge is loaded in the instrument, and the two upper and lower jaws are closed, the staple cartridge forces the top portion of the cutter, so that the cutter overcomes the elastic force of the leaf spring and returns to be in alignment with the cutter passage. At this moment, the safety mechanism is deactivated and the instrument can be fired for using.

The U.S. Pat. No. 7,055,730 discloses another safety mechanism, in which a safety block with a cutter pushing bar passage and a staple pushing bar passage is provided in the middle portion of the instrument, with the safety block being rotatable around the instrument under the action of the torsion spring. When the instrument is in an opened position, i.e., the upper jaw and the lower jaw are not closed, the safety block twists such that neither the staple pushing bar nor the cutter pushing bar are allowed to pass through their passages, thereby playing the role of safety. After the staple cartridge is loaded in the instrument, and the upper jaw and the lower jaw are closed, the staple cartridge forces the safety block such that the safety block overcomes the elastic force of the torsion spring and returns into the normal position. That is, the staple pushing bar and the cutter pushing bar align with their own passages on the safety block respectively, so that both the staple pushing bar and the cutter pushing bar are allowed to pass through the safety block. At this moment, the safety mechanism is deactivated and the instrument can be fired for using.

All of the above structures are complicated, and difficult to be manufactured and assembled, as well as costly.

SUMMARY OF THE INVENTION

An object of the present application is to provide a linear cutting stapler having a safety mechanism with simple structure.

The object of the present application will be implemented by the following technical solutions.

A linear cutting stapler is provided, including an upper jaw and a lower jaw capable of being closed or opened relative to each other, a staple cartridge being provided at a distal end of the lower jaw. The lower jaw has a U shape provided slidably with a firing piece and a cutter pushing bar. The linear cutting stapler further includes a safety mechanism including a safety member and an opening. The opening is arranged on the firing piece and used to receive the safety member. Mounting or removing of the staple cartridge may drive the safety member to move in the direction perpendicular to the axis of the lower jaw, so as to enable the safety member to be disengaged from or engaged with the opening of the firing piece.

Further, the safety member is a stop block including an engaging portion, and the outer profile of the engaging portion is identical to the inner profile of the opening of the firing piece.

Further, the stop block further includes a welding portion for being driven by the staple cartridge.

Further, the welding portion and the engaging portion are arranged at both sides of the stop block, respectively.

Further, the top surface of the welding portion is higher than that of the engaging portion.

Further, the welding portion is fixedly connected to the top surface of a leaf spring. The bottom surface of the leaf spring is fixed to the inner bottom surface of the lower jaw. The axis of the leaf spring intersects that of the lower jaw such that the bottom surface of the welding portion is higher than the bottom surface of the leaf spring.

Further, the leaf spring is fixed to both the stop block and the lower jaw by welding.

Further, the inner bottom surface of the lower jaw is provided thereon with a spacer including an elongated slot. The leaf spring passes through the elongated slot.

The present application has main beneficial effects such as a simple structure, easy to be manufactured, safe and reliable, as well as good promotion value.

Figure 1:
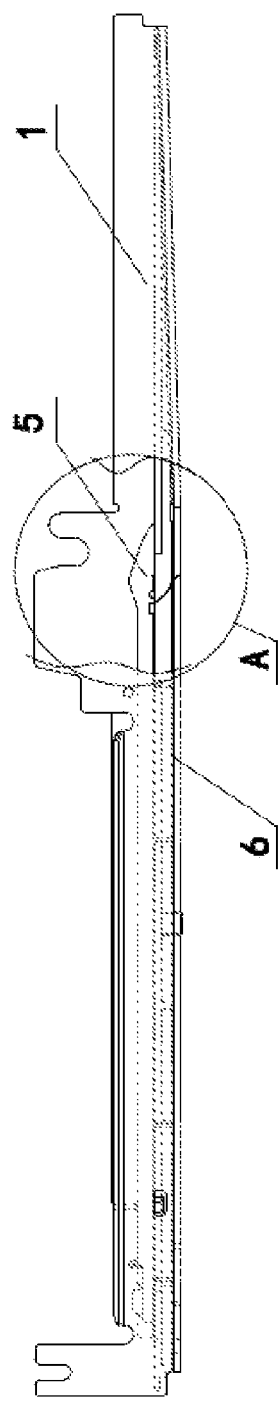
FIG. 1 is a schematic structural view of a lower jaw according to the present application, with the staple cartridge being not shown.

Reference numerals in FIGS. 1 to 5

| | |
|---|---|
| 1: lower jaw; | 11: inner bottom surface; |
| 2: staple cartridge; | 3: leaf spring; |
| 31: bottom surface; | 32: top surface; |
| 4: stop block; | 41: engaging portion; |
| 42: welding portion; | 5: firing piece; |
| 51: firing end; | 52: opening; |
| 6: spacer; | 61: elongated slot. |

DETAILED DESCRIPTION OF THE INVENTION

Figure 2:
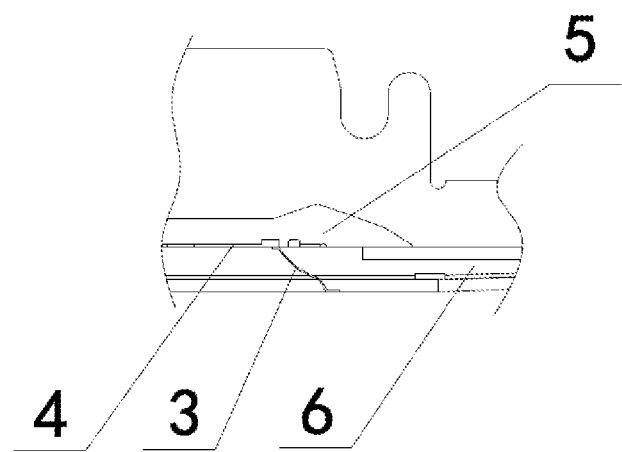
FIG. 2 is an enlarged view of part A in FIG. 1.
Figure 3:
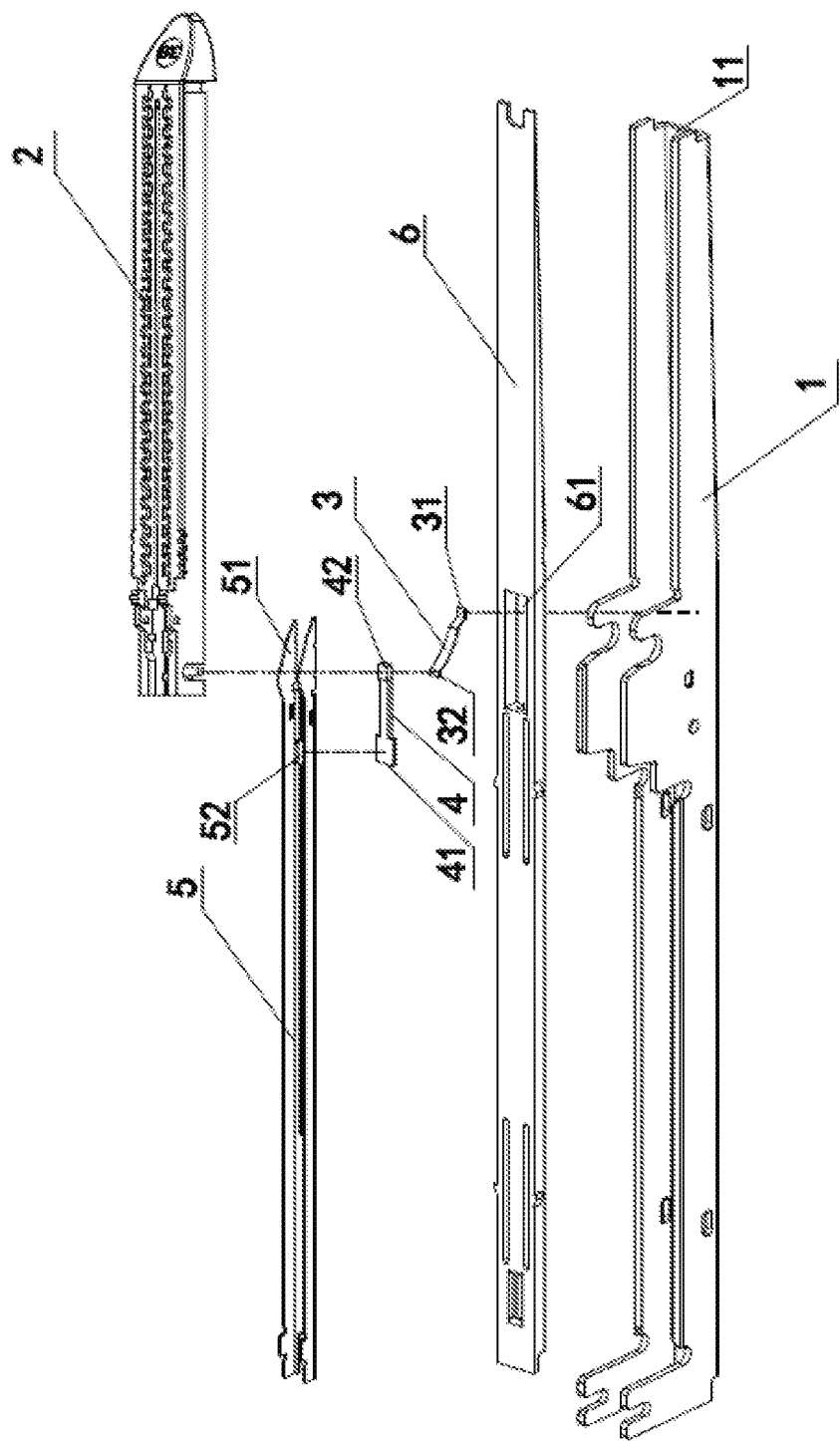
FIG. 3 is an exploded schematic view of the lower jaw according to the present application.

As shown in FIGS. 1 to 3, the present application provides a safety mechanism for a linear cutting stapler. Similar to the prior art, the linear cutting stapler includes a plastic shell, and an upper jaw and a lower jaw capable of being closed or opened relative to each other. A staple anvil (not shown) is provided at a distal end of the upper jaw, and a staple cartridge 2 is provided at a distal end of the lower jaw 1. Of course, the positions of the upper jaw and the lower jaw may be interchanged, and such a definition in the present application is only for the purpose of clarity.

The lower jaw 1 is in a U shape. A firing piece 5 and a cutter pushing bar (not shown) respectively for firing the staple pusher and cutting a tissue are slidably provided at a distal end of the lower jaw 1. In use, the tissue is placed between the staple anvil and the staple cartridge; then, the upper and lower jaws are moved towards each other to close the handle so as to enable the upper and lower jaws to clamp the tissue; and then, the firing push button arranged at the proximal ends of the upper and lower jaws is pushed to staple or cut the tissue.

The present application is characterized in that: the linear cutting stapler includes a novel safety mechanism. The safety mechanism includes a safety member and an opening 52 arranged on the firing piece 5 to receive the safety member. The opening 52 is close to the firing end 51 of the firing piece 5. In the present preferred embodiment, the safety member is a stop block 4 including an engaging portion 41. The outer profile of the engaging portion 41 is identical to the inner profile of the opening 52 of the firing piece 5. The mounting or removing of the staple cartridge 2 may drive the stop block 4 to move in the direction perpendicular to the axis of the lower jaw 1, so as to cause the engaging portion 41 of the stop block 4 to be disengaged from or engaged with the opening 52 of the firing piece 5, thereby achieving the deactivation and activation of the safety mechanism.

Figure 4:
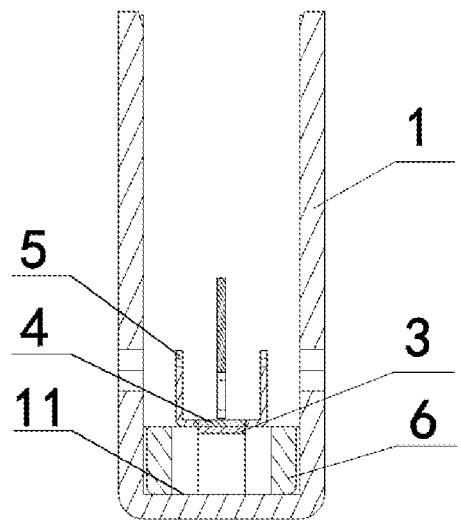
FIG. 4 is a sectional view of the lower jaw according to the present application, with the staple cartridge being unloaded.
Figure 5:
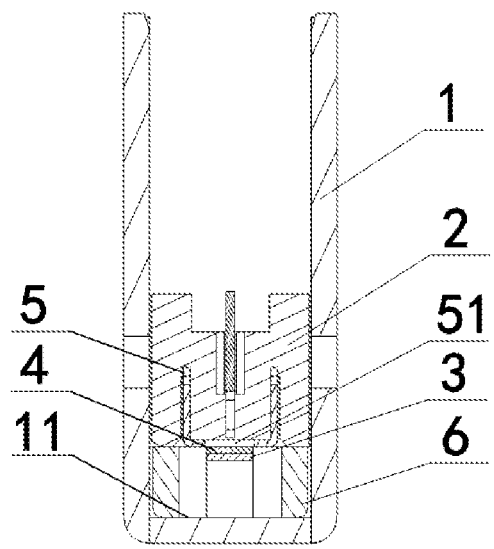
FIG. 5 is a sectional view of the lower jaw according to the present application, with the staple cartridge being loaded.

In junction with FIG. 4, the engaging portion 41 is engaged in the opening 52 to limit the movement of the firing piece 5 relative to the lower jaw 1. In conjunction with FIG. 5, the engaging portion 41 is disengaged from the firing piece 5 after being pressed by the staple cartridge 2. As a result, the firing piece 5 is movable relative to the lower jaw 1.

Further, the stop block 4 may further includes a welding portion 42 for being driven by the staple cartridge 2. The welding portion 42 and the engaging portion 41 are respectively arranged at two sides of the stop block 4. That is, in addition to the engaging portion 41, the other end of the stop block 4 may be driven by the staple cartridge 2.

Preferably, as shown in FIG. 3, the top surface of the welding portion 42 is higher than that of the engaging portion 41. In this way, when the staple cartridge 2 is mounted on the lower jaw 1, the staple cartridge 2 may preferably contact the welding portion 42. Because of the rigidity of the stop block 4, the welding portion 42 may drive the engaging portion 41 to disengage from the opening 52 of the firing piece 5.

In the present preferred embodiment, the welding portion 42 is fixedly connected to a top surface 32 of a leaf spring 3. The bottom surface 32 of the leaf spring 3 is fixed to the inner bottom surface 11 of the lower jaw 1. The axis of the leaf spring 3 intersects that of the lower jaw 1. That is, the leaf spring 3 is obliquely arranged in the lower jaw 1, and hence the bottom surface of the welding portion 42 is higher than the bottom surface 31 of the leaf spring 3, so that a height difference is kept between the welding portion 42 and the inner bottom surface 11 of the lower jaw 1 to ensure the moving distance of the stop block 4. Since in some cases, the inner bottom surface 11 of the lower jaw 1 may be provided with a spacer 6 thereon, the spacer 6 is required to include an elongated slot 61 for the leaf spring 3 to pass through. If no spacer 6 is provided, one slot may be arranged at welding joint between the leaf spring and the jaw. The leaf spring is welded on the outer surface of the jaw.

Further, in the present preferred embodiment, the leaf spring 3 is fixed to both the stop block 4 and the lower jaw 1 by welding. The instrument according to the present application has simple structure, is easy to be manufactured, safe and reliable, and has good promotion value.

The present application still includes a variety of embodiments. All the technical solutions formed by the equivalent variation or the equivalent modification fall into the protection scope of the present application.

We claim:

1. A linear cutting stapler, comprising:
an upper jaw and a lower jaw capable of being closed or opened relative to each other, a staple cartridge being provided at a distal end of the lower jaw, the lower jaw having a U shape provided slidably with a firing piece and a cutter pushing bar therein,
wherein the linear cutting stapler further comprises a safety mechanism comprising a safety member and an opening, the opening is arranged in the firing piece and configured to receive the safety member, and mounting or removing of the staple cartridge drives the safety member to move in a direction perpendicular to an axis extending from a proximal end to a distal end of the lower jaw, so as to enable the safety member to be disengaged from or engaged with the opening of the firing piece, wherein the safety member is an elongated stop block comprising an engaging portion, and an outer profile of the engaging portion is identical to an inner profile of the opening of the firing piece, wherein the stop block further comprises a portion for being welded which is driven by the staple cartridge, and the stop block is elongated in a direction substantially parallel with the lower jaw, and a proximal end of the stop block is the engaging portion, and a distal end of the stop block is the portion for being welded; and
wherein the portion for being welded is fixedly connected to a top surface of a leaf spring, a bottom surface of the leaf spring is fixed to an inner bottom surface of the lower jaw.

2. The linear cutting stapler according to claim 1, wherein the portion for being welded is on one end of the stop block and the engaging portion is on the other end of the stop block.

3. The linear cutting stapler according to claim 2, wherein a top surface of the portion for being welded is higher than that of the engaging portion.

4. The linear cutting stapler according to claim 3, wherein an axis of the leaf spring intersects that of the lower jaw such that a bottom surface of the portion for being welded is higher than the bottom surface of the leaf spring.

5. The linear cutting stapler according to claim 4, wherein the leaf spring is fixed to both the stop block and the lower jaw by welding.

6. The linear cutting stapler according to claim 5, wherein the inner bottom surface of the lower jaw is provided thereon with a spacer comprising an elongated slot, so as to allow the leaf spring to pass through the elongated slot.

* * * * *